United States Patent
Crippen et al.

(10) Patent No.: US 6,960,358 B2
(45) Date of Patent: *Nov. 1, 2005

(54) ACTIVATED CHARCOAL BASED COMPOSITION AND METHOD FOR REDUCING HANGOVER SYMPTOMS ASSOCIATED WITH THE CONSUMPTION OF ALCOHOL CONTAINING BEVERAGES

(76) Inventors: Raymond K. Crippen, 4601 Hampton Rd. at 8800 Walther Blvd., Baltimore, MD (US) 21234; Manoj Bhargava, 6250 Royal Pointe Rd., West Bloomfield, MI (US) 48322; Thomas F. Morse, 336 Wolverine Dr., Walled Lake, MI (US) 48390

( * ) Notice: Subject to any disclaimer, the term of this patent is extended or adjusted under 35 U.S.C. 154(b) by 14 days.

This patent is subject to a terminal disclaimer.

(21) Appl. No.: 10/386,941

(22) Filed: Mar. 13, 2003

(65) Prior Publication Data

US 2003/0219432 A1 Nov. 27, 2003

Related U.S. Application Data

(63) Continuation-in-part of application No. 10/042,283, filed on Jan. 11, 2002.
(60) Provisional application No. 60/260,916, filed on Jan. 12, 2001.

(51) Int. Cl.$^7$ .......................... A61K 33/10; A61K 33/44
(52) U.S. Cl. .................................. 424/687; 424/125
(58) Field of Search .................... 424/125, 602, 424/364, 687, 195.1, 725; 514/810, 811

(56) References Cited

FOREIGN PATENT DOCUMENTS

JP          04096993 A    *  3/1992

OTHER PUBLICATIONS

Living Essentials. Outsmart Hangovers With Chaser Hangover Pills [Online], [retrieved on or about Mar. 24, 2003]. Retrieved from the Internet <URL:http://www.double-chaser.com/chaser>.*

* cited by examiner

Primary Examiner—Patricia Leith
(74) Attorney, Agent, or Firm—Pillsbury Winthrop Shaw Pittman

(57) ABSTRACT

The invention provides a composition which is effective in the prevention or delay of the onset of side effects associated with alcohol consumption or the reduction or alleviation of those effects. The composition of the invention includes activated charcoal and limestone, optionally activated limestone. Optionally, the composition of the invention also includes vitamin B1 and/or other agents such as fatigue relieving agents. Preferably, the composition of the invention is provided in the form of tablets or powder encapsulated in a gelatin capsule. The composition of the invention is provided in pre-dosed quantities varying from between about 100 and 500 milligrams per dose. The invention also provides a method of reducing or alleviating the deleterious effects associated with alcohol consumption. The method includes administration, preferably multiple administration at regularly spaced intervals before, during, and after alcohol consumption of a composition containing activated charcoal and activated limestone.

19 Claims, No Drawings

ACTIVATED CHARCOAL BASED COMPOSITION AND METHOD FOR REDUCING HANGOVER SYMPTOMS ASSOCIATED WITH THE CONSUMPTION OF ALCOHOL CONTAINING BEVERAGES

CROSS-REFERENCE TO RELATED APPLICATIONS

This application claims the benefit of U.S. provisional application No. 60/260,916, filed on Jan. 12, 2001, which is hereby incorporated in its entirety by reference. This application is a continuation-in-part of application Ser. No. 10/042,283 filed Jan. 11, 2002.

FIELD OF THE INVENTION

The present invention relates to a composition which is effective in reducing the effects associated with alcohol consumption and to a method based on administering the composition to a subject in need thereof.

BACKGROUND OF THE INVENTION

As long as history has been recorded, every society has used substances that alter mood, thought and feeling. Alcohol based beverages have played a central role throughout modern history as a prominent ingredient in social and cultural gatherings. The association of alcohol based beverages with culinary enjoyment and other human celebrations have been central to the development of western culture. The role of alcohol based beverages in social human activities is increasingly spreading throughout the globe due to the adoption by populations around the world of the western lifestyle and cultural standards.

However, while consumption of alcohol based beverages in moderation has been associated with refined and sophisticated western lifestyle, abuse of alcohol and alcohol dependency (i.e., alcoholism) are increasingly a public health problem for the modern western society, and now worldwide. In the United States alone, an estimated 13 million adults exhibit symptoms of alcohol dependency due to excessive alcohol intake, and an additional 7 million abuse alcohol without showing symptoms of dependency.

Alcohol dependency and abuse are very expensive in economic and medical terms. It is estimated that alcohol abuse related expenditures will cost the U.S. well over 2 hundred billion dollars in the next year with no prospect of falling or leveling off. The social and psychological damages inflicted on individuals as consequence of alcohol abuse, for example, as more children are born with fetal alcohol syndrome and more victims fall to alcohol related accidents, homicides, suicides, etc. are immense. In view of the staggering statistics associated with alcohol abuse, most, if not all efforts concerned with the effects of alcohol focused on the treatment of alcohol abuse and alcoholism. While those efforts are important and should be pursued, they should not overshadow the importance of the positive effects of moderate consumption of alcohol within ancestral social and cultural norms.

The less dramatic effects of alcohol when consumed in moderation have received little or no interest. There have been very few remedies rationally developed for addressing the effects of moderate alcohol consumption. Those effects include alcohol related "hangover" which is generally characterized by a headache, tremulousness, nausea, sour stomach, diarrhea, fatigue and decreased cognitive or visual-spatial skills.

The symptoms referred to as hangover are believed to be connected to dehydration, hormonal alterations, de-regulation of cytokine pathways and other toxic effects of alcohol. Dehydration is believed to be one of the primary causes of hangover. As alcohol is ingested, ethanol is introduced into the blood stream. In the body, alcohol and its metabolites are identified as toxins and are therefore broken down to less harmful chemical entities. In the body, the liver and kidneys are the organs where most of toxin processing takes place. In order for toxins to be processed adequately by the liver and kidneys, they must be dissolved in water. When the amount of toxins generated by alcohol consumption is higher than the amount of water available in the stomach, water is drawn from other areas of the body where water may be available. In order to process excessive amounts of toxins associated with alcohol consumption, water is generally drawn from the blood, the lymphnodes and the brain. Intensive use of the water available in the body in the processing of toxins results in dehydration, which in turn may result in effects ranging from mere headaches to serious harm to the brain, kidneys, liver, lymphnodes and other vital parts of the human body.

Other effects of alcohol consumption are associated with the presence of congeners generated during the preparation of alcohol beverages, particularly in fermentation processes. Another source for the effects of alcohol consumption is associated with the build up of acetaldehyde during the metabolism of alcohol by the liver and kidneys. Alcohol breakdown in the liver involves two steps which are catalyzed by two different enzymes. In the first step, the enzyme alcohol dehyrogenase (ADH) converts alcohol into extremely toxic acetaldehyde. In the second step, the enzyme dehyrogenase (ALDH) converts the acetaldehyde into harmless acetate.

When acetaldehyde is produced at a faster rate than it is converted to acetate, excess acetaldehyde accumulates in the liver which produces an extreme visible reaction. The visible violent effects of acetaldehyde accumulation on the body has resulted in particular attention to the treatment of symptoms associated with acetaldehyde accumulation in the liver. Most studies have focused on using vitamin B6 to help reduce the amount of acetaldehyde accumulated in the liver due to alcohol ingestion as vitamin B6 is believed to be a co-factor that facilitates the conversion of acetaldehyde by ALDH into acetate. However, it has been shown that vitamin B6 is generally available in sufficient amounts in the body upon consumption of alcohol and therefore the administration of high doses of B6 have not resulted in significant reduction of the side effects of alcohol consumption. However, studies have shown that vitamin B1 required for (ADH) is potentially available in insufficient amounts to both supply the required Thiamine (B1) for the essential oxygen-dependent part of the metabolism of alcohol and supply the required vitamin B1 to the body. The net affect is in addition to making it harder to breakdown the alcohol into the harmless acetate for efficient removal from the body, high blood alcohol levels can potentially reduce the vitamin B1 supply to the brain. Long term effects of vitamin B1 deficiency in the brain can cause severe health problems.

Another approach for reducing the undesirable effects of alcohol consumption has focused on the removal of alcohol and its metabolites from the blood stream through absorption by alcohol absorbing materials. Specifically, U.S. Pat. No. 4,594,249, the contents of which are hereby incorporated by referenced in their entirety, discloses the use of activated charcoal in alleviating the effects of consumption of alcohol containing beverages. The '249 patent discloses that the effects of alcohol consumption may be reduced by administering to a subject activated charcoal in amounts varying between 5 and 15 milligrams per kilogram of weight of the subject. However, administration of activated charcoal alone has provided only limited reduction of the hangover symptoms associated with alcohol consumption. More effective reduction of those effects would necessitate the injection of substantially larger quantities of activated charcoal.

The effective use of activated charcoal in the treatment of the effects of alcohol consumption may require the administration of high doses in the range of 50 grams or more which must be provided in water suspension form. However, charcoal suspension adheres to the mucosal surfaces of the throat, and gives a chalk like taste which is objectionable and may reduce the desirability of intake of activated charcoal. The limited effectiveness of activated charcoal at doses that are adequate for administration in tablet or capsule form essentially has resulted in a halt in the efforts to develop methods of reducing the effects of alcohol consumption based on activated charcoal.

Thus, there remains a need for compositions and methods based on activated charcoal, yet presenting a significantly enhanced effect in reducing the hangover symptoms associated with alcohol consumption without the need for increased doses of activated charcoal to be administered to a subject beyond the quantities adequate for capsule and tablet packaging. It is therefore an object of the present invention to provide a composition which is based on activated charcoal and which allows a significant reduction in the effects of alcohol consumption while administrating activated charcoal in small doses which are compatible with tablet and capsule packaging and administration.

SUMMARY OF THE INVENTION

The present invention is based on the unexpected discovery that the combination of activated charcoal with limestone, optionally activated limestone allows for the preparation of a composition which is significantly more effective in reducing the effects of alcohol consumption and which allows administration of activated charcoal in doses that are compatible with the preparation of the composition in tablet or capsule form.

Thus, in its broadest embodiment, the present invention provides a composition for the prevention or delay of the onset of the side effects associated with alcohol consumption or the reduction or alleviation of said side effects, wherein said composition comprises activated charcoal and limestone, optionally activated limestone. Optionally, the composition may further include vitamin B1. Typically, the composition will comprise up to 80 wt. % activated charcoal, for instance more than 20 wt. % and preferably between 30 and 60 wt. % and more preferably up to 45 wt. % activated charcoal. The composition may also include up to 80 wt. % activated limestone, for instance 20 wt. %, 40 wt. % or 60 wt. % and preferably the activated limestone will be present in the composition in a range between 55 wt. % and 75 wt. %. and more preferably between 40 and 70 wt. %.

Other components with beneficial effects in reducing the side effects of alcohol consumption that may be included in the composition of the invention include rehydrating agents, agents capable of reducing alcohol dependency, such as olanzapine, fatigue relieving agents, such as L-methionine or a biologically acceptable salt thereof, or a biologically acceptable magnesium salt, folic acid, vitamin B12 or mixture thereof.

In a second embodiment, the invention provides a method for alleviating the undesirable "hangover" effects associated with alcohol ingestion comprising administering to a subject a composition comprising activated charcoal and limestone, optionally activated limestone.

DETAILED DESCRIPTION OF PREFERRED EMBODIMENTS OF THE INVENTION

The present invention is based on the unexpected discovery that a composition comprising activated charcoal and limestone, optionally activated limestone allows for more effective and faster alleviation and reduction of the effects of alcohol ingestion compared to administering a composition based on activated charcoal alone. The enhanced activity of the composition of the invention allows for the preparation of activated charcoal based compositions in the form of tablets or capsules containing the composition in the form of powder. In particular, the invention is based on the discovery that activated charcoal and activated limestone synergistically combine to significantly reduce the presence of alcohol or its harmful metabolites in the blood stream.

It is believed that the combination of activated charcoal and limestone, optionally activated limestone allows for significantly enhancing the adsorption properties of the composition of the invention. In significantly increasing the efficacy of the composition of the invention while using activated charcoal in a quantity of between 5 to 15 milligrams per kilogram of body weight allows for the formulation of the composition of the invention in acceptable forms, such as tablet form and encapsulated powder. In effect, with the addition of limestone, optionally activated limestone, compositions based on activated charcoal are now much more desirable in the alleviation of the symptoms associated with alcohol ingestion. Recognizing that the composition may be incorporated into a variety of delivery systems, the active ingredients, i.e, the activated charcoal and the activated limestone, can be present in amounts of between 20 and 80 wt. % activated charcoal (correspondingly between 20 and 80 wt. % activated limestone), preferably 30 and 50 wt. % activated charcoal with the balance activated limestone.

Activated charcoal is a fine, black, insoluble powder, without taste or odor. After preparation by combustion of organic material such as wood, it is activated by an oxidizing gas flow at high temperature. This process creates a solid having an internal network of pores presenting an internal surface area which is much larger than the external surface area of the solid. For example, the total surface area of activated charcoal is on the order of 1,000 meters per gram while the total full volume is about 1 cubic centimeter per gram. Activated charcoal is commercially available in many different grades and under a variety of brand names.

In conjunction with activated charcoal, the composition of the invention also comprises limestone, optionally activated limestone. Limestone is a sedimentary rock composed mainly of calcium carbonate ($CaCO_3$), usually in the form of calcite or aragonite. Limestone may contain considerable amounts of magnesium carbonate (dolomite) as well; minor constituents also commonly present include clay, iron carbonate, feldspar, pyrite, and quartz. Most limestones have a granular texture. Their constituent grains range in size from 0.001 mm (0.00004 inch) to visible particles. In many cases, the grains are microscopic fragments of fossil animal shells. Limestone has two origins: (1) biogenic precipitation from sea water (autochthonous limestone), the primary agents being lime-secreting organisms and foraminifera; and (2) mechanical transport and deposition of preexisting limestones (allochthonous limestone), forming clastic deposits. Limestone has long fascinated earth scientists because of its rich fossil content. Limestone is commercially available from various sources, including Prime PVC Inc.

Although compositions according to the invention may be administered to subjects in a variety of forms, they are preferably given in the form of loose powder encapsulated in a water soluble encapsulating material. Capsules may contain convenient dosage quantities in the range from 100 to 800 milligrams, preferably 100 to 500 milligrams, per capsule. Compositions of the invention may also be administered in tablet form preferably in dose sizes of from about 50 to 300 milligrams per tablet. The effect of combining activated charcoal with limestone, optionally activated limestone according to the invention may also be achieved by administering two types of tablets or capsules, one type of tablet or capsule containing activated charcoal and the other type of tablet or capsule containing limestone or activated limestone.

Compositions according to the invention including-activated charcoal and limestone, optionally activated limestone, and optionally other ingredients such as Vitamin B1, can be prepared according to various methods. Particularly, the composition of the invention can be prepared according to the method disclosed in U.S. Pat. No. 5,496,566, the contents of which are hereby incorporated by reference in their entirety.

For the effective alleviation of the adverse side effects of alcohol ingestion, the composition of the invention is preferably packaged in pre-dosed quantities and in a form suitable for self-administration. Preferably, a first dose, in the form of a tablet or capsule containing the composition of the invention is taken by a subject shortly before or at the time of beginning to drink an alcoholic beverage. The pre-dosed tablet or capsule preferably contains between about 5 and 15 milligrams of the composition of the invention per kilogram of body weight. For example, a standard dose of the composition of the invention may contain two tablets or capsules each containing 300 to 600 milligrams, preferably 400 milligrams, of the composition of the invention.

Optimum effects of the composition of the invention in reducing or preventing the onset of the deleterious effects associated with alcohol ingestion includes self-administration of one dose of the composition of the invention in intervals of one to three hours during moderate alcohol consumption or one to two hours during heavy drinking. When alcohol is consumed, it is ingested into the digestive tract and is quickly absorbed into the circulatory system. The administration of a dose of a composition of the invention including activated charcoal and limestone (preferably activated limestone), and optionally, vitamin B1 during alcohol consumption reduces but does not totally eliminate the absorption of alcohol into the bloodstream. Thus, the more desirable effects associated with alcohol consumption such as the feeling of euphoria associated with the presence of alcohol and its metabolites in the bloodstream is still maintained while the deleterious effects associated with an excessive presence of alcohol or its metabolites in the bloodstream are significantly reduced or eliminated. Excessive amounts of alcohol and/or its metabolites are absorbed by the activated charcoal and activated limestone of the composition of the invention while the optional other components help reduce the effects of alcohol and its metabolites through mechanisms other than the absorption or adsorption of alcohol or its metabolites.

It is highly desirable to administer one or few final doses of the composition of the invention at the end of the period of alcohol consumption. The composition administered after alcohol intake is terminated helps clear ethanol and its metabolites from the circulatory system. It is believed that the adsorption by the composition of the invention of alcohol, its metabolites, and congeners associated with its production, produces a gradient of concentration of these undesirable components in favor of movement of the compounds back into the gut. Therefore, the quantity of alcohol, its metabolites and congeners present in the bloodstream is significantly reduced which in turn results in significant reduction in the deleterious effects associated with alcohol consumption, particularly those known to be associated with the "hangover" effect.

The methods of the present invention may be used as a prophylactic treatment.

EXAMPLES

Example 1

In order to show the efficacy of the composition of the invention in significantly reducing blood alcohol levels upon the ingestion of alcohol based beverages, the composition of the invention was administered to a group of volunteers who were provided with alcohol beverages and subjected to blood alcohol analysis through breathalyzer measurements. The first group (subjects A–D) consisted of 4 females who were provided with various alcohol beverages and two capsules containing about 850 milligrams of a composition containing activated charcoal and activated limestone according to one embodiment of the invention, which were orally self-administered with the second drink. The second group (subjects E and F) consisted of two males, each took two capsules, each containing 900 milligrams of the composition of the invention immediately after the last drink. The characteristics of the volunteers and the results obtained during this experiment are summarized in Tables 1–3.

TABLE 1

| Subject | Age | Weight | Height | Gender | Time of last meal | Time Subject began drinking |
| --- | --- | --- | --- | --- | --- | --- |
| A | 35 | 160 | 5'7" | F | 8:00 am | 5:30 pm |
| B | 36 | 128 | — | F | 3:30 pm | 5:30 pm |
| C | 35 | 120 | — | F | 3:30 pm | 5:30 pm |
| D | 37 | 122 | — | F | 2:00 pm | 4:00 pm |
| E | 47 | 165 | — | M | 12:30 pm | 2:30 pm |
| F | 31 | 170 | — | M | 12:30 pm | 2:30 pm |

TABLE 2

| Subject | Time Subject began drinking | Type of Drink consumer | Time Subject stopped drinking | No. of Drinks consumed |
| --- | --- | --- | --- | --- |
| A | 5:30 pm | Hurricanes - dark and light rum | 9:30 pm | 9 |
| B | 5:30 pm | Rum | 9:30 pm | 6 |
| C | 5:30 pm | Tequila | 9:30 pm | 3 |
| D | 4:00 pm | Beer and rum | 9:30 pm | 10 |
| E | 2:30 pm | Beer | 4:35 pm | 6 |
| F | 2:30 pm | Beer | 4:35 pm | 6 |

TABLE 3

BREATHALYZER READING

| Subject | at middle of drinking session | after 20 min. of last drink | after 50 min. of last drink | after 1 hr. of last drink | after 1 hr. and 15 min. of last drink | after 1 hr. and 30 min. of last drink |
|---|---|---|---|---|---|---|
| A | .11 | .7 | .04 | .03 | .02 | .00 |
| B | .4 | .2 | .00 | — | — | — |
| C | .3 | .2 | .00 | — | — | — |
| D | .19 | .15 | .09 | .05 | .03 | .02 |
| E* | — | .15 | .17 | .15 | .14 | .12 |
| F** | — | .09 | .12 | .1 | .09 | .08 |

*The last reading for subject E was conducted 2 hours and 30 minutes of last drink and indicated a blood alcohol level of 0.13.
**The blood alcohol level for subject F decreased to 0.06 after 2 hours and 30 minutes of last drink and to 0.03 after 4 hours and 15 minutes of last drink.

The results shown in Table 3 show that the composition of the invention is highly effective when taken during the course of drinking session compared to taking the composition at the end of the drinking session. Results similar to those obtained with the subjects who took the composition of the invention during the drinking session would be obtained if the composition is administered prior to the start of the drinking session. However, when the composition is taken before the start of the drinking session the effect of alcohol is drastically reduced and the subject may not experience the euphoria associated with the drinking of alcoholic beverages. Thus, in a preferred embodiment the composition of the invention is administered shortly after the start of the drinking session (after the first drink), to keep the blood alcohol level low while at the same time allowing the subject to experience some of the euphoria and nice feeling associated with moderate alcohol consumption.

In order to test the efficacy of the composition in reducing or eliminating hangover-related symptoms a randomized, blind, placebo-controlled trial was implemented on nine male and female subjects.

Initially, 10 subjects entered the test protocol, 1 was disqualified because the subject did not show any reaction to alcohol consumption. The remaining 9 subjects participated in four evening sessions, as set forth in Table 4, conducted in random order. The drinks consumed approximately every half hour consisted of domestic wine (approximately 13.5 to 14% of alcohol by volume) in an volume/subject's body weight equal to approximately 0.25 g alcohol/kg of body weight (a total of 1 g alcohol/kg of body weight was administered over a 2 hour period) and dosage administered, as indicated in Table 4, during the session equals 2 capsules (450 milligrams capsules comprising approximately 35 wt. % activated charcoal and approximately 65 wt. % activated limestone).

TABLE 4

| Session Sequence | 1st Drink | 2nd Drink | 3rd Drink | 4th Drink | Final Dosage |
|---|---|---|---|---|---|
| A | P-dosage | — | P-Dosage | — | P-Dosage |
| B | TC-Dosage | — | P-Dosage | — | P-Dosage |
| C | P-dosage | — | TC-Dosage | — | P-Dosage |
| D | TC-dosage | — | P-Dosage | — | TC-Dosage |

Table Notes:
TC => Test Composition
P => Placebo

Measurements were performed based on subjective symptom scores for headache, fatigue, dry mouth, diarrhea, anorexia, nausea, tremulousness and sense of overall well being were recorded the morning after the session (between 8:30 and 9:30 am). In almost all cases, the severity of the symptoms was reduced. Table 5 summarizes the results based on the data collected for the double dosage session (sequence D) vs. the placebo session (sequence A).

TABLE 5

| | Average Placebo Score | Average Double Dosage Score |
|---|---|---|
| Headache | 2 | 1.4 |
| Fatigue | 3 | 1.6 |
| Dry mouth | 3.4 | 2 |
| Diarrhea | 1.3 | 1 |
| Anorexia | 1.3 | 1.3 |
| Nausea | 1.6 | 1.3 |
| Tremulousness | 1.3 | 1.1 |

1 = Best (no symptoms) and 5 = Worst (severe symptoms)

| Well being** | 3.2 | 4.6 |
|---|---|---|

*5 = Best and 1 = Worst

From the above reported results, it can be concluded that administration of the activated calcium carbonate/charcoal was associated with significant reduction in severity of most alcohol-related hangover symptoms in those who are subject to hangovers.

Example 2

Study Participants

Thirty-five participants were selected for a prospective, randomized, placebo-controlled, double-blind, cross-over clinical study of a composition of the present invention (the "test formulation"). Participants were chosen from those answering radio ads for this experiment, and were paid $100 for their participation. Potential participants were screened prior to participation, and were excluded for the following: non-compliance with testing and/or treatment regimens, inability to tolerate the test formulation or placebo material, age less than 21 or over 50, alcohol-related dysfunctional problems (including involvement in alcohol-related treatment, or elevated liver enzymes), women who were nursing or pregnant or who were at a moderate-to-high risk for getting pregnant, medications that could be altered by the test formulation; individuals taking medications within four hours of taking the treatment regimen, moderate to severe co-morbid disease (including cardiac, pulmonary, renal, hepatic, or active cancer), or alcohol abuse. However the following traits or symptoms did not result in the exclusion of a participant: self-reported post-alcohol distress syndrome (acute setting), or persons who typically consume at least two drinks a week, but no more than fourteen weekly.

Table 6 shows baseline health characteristics of the participants involved in this study, and Table 7 shows a historical record of the participants' alcohol consumption. In Table 8, the age, gender, risk score and weight of each participant, along with the administered form of alcohol are reported. Table 9 shows the number of study participants falling within each risk score.

TABLE 6

BASELINE HEALTH CHARACTERISTICS OF TEST PARTICIPANTS

| Characteristic | Number of Participants Reporting | Percentage of Participants |
|---|---|---|
| Diabetic | 1 | 2.9 |
| Hypertension | 4 | 11.4 |
| Thyroid Disease | 1 | 2.9 |
| COPD | 0 | 0 |
| Cardiac Conditions | 1 | 2.9 |
| Major Injury | 1 | 2.9 |
| Major Surgery | 6 | 17.1 |
| Renal Conditions | 0 | 0 |
| Liver Conditions | 1 | 2.9 |
| Gastro Intestinal Conditions | 2 | 5.7 |
| Cancer | 1 | 2.9 |
| Elevated Cholesterol | 4 | 11.4 |
| Caffeine >3 Cups | 16 | 45.7 |
| Former Smoker | 14 | 40 |

TABLE 6-continued

BASELINE HEALTH CHARACTERISTICS OF TEST PARTICIPANTS

| Characteristic | Number of Participants Reporting | Percentage of Participants |
|---|---|---|
| Current Smoker | 14 | 40 |
| Female | 19 | 54.3 |
| Depression | 0 | 0 |

TABLE 7

HISTORICAL ALCOHOL CONSUMPTION AMONG TEST PARTICIPANTS*

| Number of Drinks/Week | Number of Participants Reporting | Percent |
|---|---|---|
| 0 | 2 | 5.7 |
| 1 | 2 | 5.7 |
| 2 | 3 | 8.6 |
| 3 | 8 | 22.9 |
| 4 | 4 | 11.4 |
| 5 | 6 | 17.1 |
| 6 | 3 | 8.6 |
| 7 | 6 | 17.1 |
| 8 | 1 | 2.9 |
| | 35 | 100 |

*For comparison, according to the 1997 Ninth Special Report to the United States Congress on Alcohol and Health (pp 3–4), for the year 1993, the U.S. average per capita consumption is approximately eleven (11) drinks per weeks.

TABLE 8

PARTICIPANT DEMOGRAPHICS, RISK SCORE, TYPE AND AMOUNT OF ALCOHOL CONSUMED, AND HANGOVER DIFFERENCE SCORE

| | Age | Gender | Weight | Historical Alcohol Consumption (drinks/week) | Risk Score | Choice of Liquor in study | Number of Drinks Consumed in study | Hangover Difference (See Below) |
|---|---|---|---|---|---|---|---|---|
| 1 | 28 | Male | 200 | 4 | 2 | Wine | 4 | 1 |
| 2 | 28 | Female | 161 | 3 | 1 | Wine | 4 | 0 |
| 3 | 51 | Female | 168 | 5 | 4 | Wine | 5 | -2 |
| 4 | 48 | Male | 220 | 7 | 7 | Tequila | 10 | 7 |
| 5 | 41 | Female | 210 | 3 | 4 | Tequila | 8 | 4 |
| 6 | 28 | Male | 265 | 7 | 5 | Whiskey | 12 | 0 |
| 7 | 42 | Female | 250 | 5 | 4 | Vodka | 11 | 6 |
| 8 | 46 | Male | 180 | 7 | 5 | Beer | 9 | 1 |
| 9 | 22 | Female | 160 | 5 | 2 | Beer | 7 | 4 |
| 10 | 31 | Male | 254 | 3 | 2 | Beer | 11 | 1 |
| 11 | 47 | Male | 212 | 7 | 5 | Whiskey | 8 | 6 |
| 12 | 47 | Female | 171 | 6 | 8 | Beer | 6 | 4 |
| 13 | 42 | Female | 160 | 5 | 2 | Wine | 5 | 2 |
| 14 | 26 | Male | 148 | 2 | 0 | Wine | 4 | 4 |
| 15 | 45 | Male | 170 | 2 | 0 | Beer | 5 | 3 |
| 16 | 49 | Female | 300 | 1 | 4 | Tequila | 5 | 2 |
| 17 | 50 | Female | 174 | 4 | 5 | Kamora | 7 | 5 |
| 18 | 40 | Female | 160 | 4 | 2 | Beer | 6 | -1 |
| 19 | 41 | Male | 260 | 6 | 1 | Beer | 10 | 1 |
| 20 | 39 | Female | 245 | 1 | 1 | Tequila | 9 | 4 |
| 21 | 26 | Female | 230 | 1 | 2 | Kamora | 6 | 3 |
| 22 | 36 | Male | 186 | 1 | 3 | Brandy | 7 | 2 |
| 23 | 37 | Female | 140 | 5 | 5 | Kamora | 6 | 1 |
| 24 | 48 | Female | 145 | 3 | 6 | Rum | 6 | 4 |
| 25 | 32 | Male | 220 | 8 | 0 | W. Russian | 8 | 7 |
| 26 | 25 | Male | 220 | 6 | 2 | Tequila | 8 | 4 |

TABLE 8-continued

PARTICIPANT DEMOGRAPHICS, RISK SCORE, TYPE
AND AMOUNT OF ALCOHOL CONSUMED, AND HANGOVER
DIFFERENCE SCORE

|  | Age | Gender | Weight | Historical Alcohol Consumption (drinks/week) | Risk Score | Choice of Liquor in study | Number of Drinks Consumed in study | Hangover Difference (See Below) |
|---|---|---|---|---|---|---|---|---|
| 27 | 42 | Female | 190 | 3 | 3 | Brandy | 7 | 3 |
| 28 | 52 | Male | 214 | 7 | 7 | Beer | 8 | 1 |
| 29 | 29 | Female | 195 | 3 | 3 | Beer | 9 | 3 |
| 30 | 24 | Female | 160 | 3 | 3 | Tequila | 7 | 5 |
| 31 | 28 | Female | 120 | 3 | 3 | Tequila | 6 | 1 |
| 32 | 31 | Male | 220 | 4 | 1 | Beer | 8 | 2 |
| 33 | 38 | Male | 180 | 7 | 1 | Wine | 5 | 2 |
| 34 | 35 | Male | 175 | 5 | 1 | Wine | 5 | −2 |
| 35 | 33 | Female | 125 | 2 | 0 | Wine | 4 | 1 |

TABLE 9

NUMBER OF STUDY PARTICIPANTS AT EACH RISK SCORE

| Risk Score | Number of Participants | Percent |
|---|---|---|
| 0 | 4 | 11.4 |
| 1 | 6 | 17.1 |
| 2 | 7 | 20.0 |
| 3 | 5 | 14.3 |
| 4 | 4 | 11.4 |
| 5 | 5 | 14.3 |
| 6 | 1 | 2.9 |
| 7 | 2 | 5.7 |
| 8 | 1 | 2.9 |
|  | 35 | 100 |

Low Risk 0–2
Intermediate Risk 3–5
High Risk 6+

Study Design and Results

The participants where next divided into two groups and were administered alcohol at the intervals depicted in Table 10. Randomization determined which participants were assigned to each group. One group of participants received a test formulation consisting of the formulation listed in Table 11, while the other group received a placebo that was similar in appearance (size, shape, color) to the test formulation, but only contained the inert substances listed in Table 12. Both were dispensed in unlabeled white bottles and the study participants, study coordinator, epidemiologist, and research nurse performing the study were blinded to the randomization scheme. After two weeks, the groups were switched and the test was performed again. Follow-up testing was conducted after each drinking episode. Two individuals reported becoming "sick" immediately after one of their drinking episodes. Both individuals did so while on placebo. Additionally there were no clinical differences during two episodes (test formulation versus placebo) for systolic and diastolic blood pressure.

TABLE 10

DRINKING AND DOSING SCHEME USED

| Time (min) | Action |
|---|---|
| −2 | 2 capsules with water |
| 0 | Drink 1 |
| 30 | Cup of water |
| 45 | Drink 2 |
| 60 | Cup of water |
| 90 | Drink 3 |
| 135 | 2 capsules with water |
| 135 | Drink 4 |
| 150 | Cup of water |
| 180 | Drink 5 (if scheduled) |
| 225 | Drink 6 (if scheduled) |
| 270 | Drink 7 (if scheduled) |

TABLE 11

COMPOSITION OF TEST FORMULATION

| Component | Weight Percent |
|---|---|
| Activated Charcol | ≈35% |
| Activated Limestone | ≈65% |
| Other: Sucrose, cellulose, croscarmellose sodium, stearic acid, magnesium stearate | Less than 2% |

TABLE 12

COMPOSITION OF PLACEBO

| Component | Weight Percent |
|---|---|
| Activated Charcol | 0% |
| Activated Limestone | 0% |
| Sucrose | 99% |
| Other: Cellulose, croscarmellose sodium, stearic acid, magnesium stearate | Less than 2% |

Following each drinking session, researchers gathered evidence from participants to evaluate various symptoms. The symptoms were selected as indicators of the effects of moderate alcohol consumption, acute alcoholic toxicity and gastrointestinal sequelia. Identical questions for both the placebo and test groups were asked. Answers from survey questions were coded from 0 to 10, where 0 represented no symptoms and 10 represented feeling the worst one could.

For example, the question designed to determine bloating read as follows:

"Indicate how you felt for the first couple of hours that you were awake this morning."

| For Bloating | | | | | | | | | | |
|---|---|---|---|---|---|---|---|---|---|---|
| 0 | 1 | 2 | 3 | 4 | 5 | 6 | 7 | 8 | 9 | 10 |
| 0 = Not at all | | | | | | | | | | Extreme |

In order to determine the improvement, the improvement value was calculated as follows:

$$P.R. - T.R. = I.V.$$

wherein P.R. represents "Placebo Response", T.R. represents "Treatment Response" and I.V. represents "Improvement Value".

For example, a participant answering the question about bloating following episodes 1 and 2 gave the following responses:

| Time | Response |
|---|---|
| Episode 1 (placebo) | 5 |
| Episode 2 (product) | 2 |

The subtraction of the responses yields an Improvement Value for this participant on this question:

$$5 - 2 = \text{an } I.V. \text{ of } 3.$$

Mean improvement value among the participants is reported in Table 13. Each variable (symptom) measured contains thirty-five data points, even if during the placebo episode, the participant rated a given parameter as non-existent ("0"). For each parameter, the means were all positive, indicating an improvement in this parameter during the episode while taking the test formulation. Note that the minimum scores for all but three parameters had negative numbers meaning that some participants had better reactions while taking the placebo. Differences in the means between the treatment and placebo groups were analyzed using the t-test. See Bailar, J. C. and Mosteller, F. *Medical Uses of Statistics*, Second Edition, New England Journal of Medicine Books, Boston, Mass. (1992), Chapters 4, 12 and 13; Altman, D. G., *Practical Statistics for Medical Research*, Chapman and Hall, London (1991), Chapters 9 and 10.

TABLE 13

MEAN SCORE IMPROVEMENT FOR VARIOUS SYMPTOMS BETWEEN TEST FORMULATION AND PLACEBO

| Parameter | Mean | Std. Dev. | Minimum | Maximum |
|---|---|---|---|---|
| Headaches | 2.83 | 2.33 | −3 | 9 |
| Fatigue/Energy | 2.57 | 2.84 | −5 | 8 |
| "Hangover" | 2.54 | 2.29 | −2 | 7 |
| Light Sensitivity | 1.03 | 2.02 | −1 | 7 |
| Sound Sensitivity | 1.06 | 1.98 | 0 | 6 |
| Irritated Eyes (Red Eyes) | 1.69 | 2.34 | −4 | 6 |
| Dry Mouth | 2.06 | 2.69 | −4 | 6 |
| Nausea | 1.37 | 2.49 | −5 | 7 |
| Vomiting | 0.40 | 1.80 | 0 | 10 |
| Diarrhea | 0.86 | 2.16 | −3 | 6 |
| Bloating | 1.66 | 2.27 | −2 | 10 |
| Cramping | 1.37 | 2.26 | 0 | 8 |
| Shaking | 0.49 | 1.52 | 0 | 8 |
| Sweating | 1.89 | 1.86 | −3 | 8 |
| Dizziness | 1.66 | 2.48 | −3 | 10 |
| Room is "Spinning" | 1.00 | 2.39 | −3 | 10 |
| Mood Swings | 0.80 | 1.91 | −3 | 6 |

TABLE 13-continued

Percent improvement (PI) was calculated as follows:

$$\frac{P.R. - T.R.}{P.R.} \times 100 = P.I$$

For example, using the previous example's value, the percent improvement may be calculated as follows:

$$[(5-2)/5]*100 = 60\% \text{ improvement}$$

The PI only took into account those with reported symptoms and their respective changes. The overall PI for each parameter was positive, indicating there was an improvement while taking the test formulation, and these results are reported in Table 14.

TABLE 14

PERCENTAGE IMPROVEMENT FOR VARIOUS SYMPTOMS BETWEEN TEST FORMULATION AND PLACEBO

| Parameter | Number of Participants | Mean (%) | Std. Dev. (%) |
|---|---|---|---|
| Headaches | 33 | 70.4 | 42.5 |
| Fatigue/Energy | 35 | 29.3 | 88.4 |
| "Hangover" | 35 | 54.5 | 59.6 |
| Light Sensitivity | 12 | 62.9 | 63.6 |
| Sound Sensitivity | 10 | 78.6 | 34.3 |
| Irritated Eyes (Red Eyes) | 32 | 38.6 | 88.4 |
| Dry Mouth | 33 | 45.0 | 56.6 |
| Nausea | 21 | 36.4 | 131.3 |
| Vomiting | 2 | 100.0 | 0 |
| Diarrhea | 10 | 20.0 | 146.2 |
| Bloating | 22 | 70.0 | 74.9 |
| Cramping | 18 | 52.0 | 105.8 |
| Shaking | 5 | 95.0 | 11.2 |
| Sweating | 30 | 67.4 | 74.0 |
| Dizziness | 25 | 63.2 | 103.4 |
| Room is "Spinning" | 16 | 55.0 | 120.6 |
| Mood Swings | 12 | 30.5 | 134.5 |

Vigil

This was a computer-administered test procedure. The participant must sustain attention to the computer screen for eight (8) minutes, pressing a key for targets (the letter "k") but not responding to non-targets (any other letter). The screen background is dark and a random single letter appears in the middle of the screen at a standard interval.

The scoring was based on the number of correct responses, the number of incorrect responses (to non-targets), relative accuracy, and reaction time. As before, the mean value was calculated by subtracting the results of the placebo group from those of the test formulation group. These results are shown in table 15. The mean represents the improvement during treatment with the test formulation.

TABLE 15

COGNITIVE DATA: RESULTS OF THE VIGIL COMPUTER TEST

| Parameter | Participants | Mean | Std. Dev. | Min, Max | P-value |
| --- | --- | --- | --- | --- | --- |
| Misses | 27 | 2.59 | 2.19 | −2, +8 | 0.0001 |
| Extra Keystrokes | 27 | 3.03 | 2.89 | −3, 9 | 0.0001 |
| Total Errors | 27 | 5.63 | 4.56 | −5, 14 | 0.0001 |

Statistical Significance

Statistical significance is measured by a p-test, which indicates the likelihood that the result would be the same or better in subsequent clinical trials by chance alone. The p-test generates a p-value, and the p-value generally considered significant in the statistics community is less than 0.05 (5%). An outcome containing this p-value would indicate that there is a less than 5% chance that the outcome was a result of chance alone and had nothing to do with the product's effectiveness. See, e.g., Meinert, CL. *Clinical Trials: Design, Conduct, and Analysis*. New York: Oxford University Press; 1986.

In this study, the following criteria were set prior to the analysis:

| | |
| --- | --- |
| Highly Significant Results: | p-value < 0.05 |
| Significant Results: | p-value < 0.10 |
| Statistical Trend: | p-value < 0.15 |

While the present invention has been described in illustrative terms, the scope thereof is only limited by the claims which follow.

What is claimed is:

1. A method of preventing, reducing, alleviating, or delaying the onset of at least one symptom associated with alcohol consumption, comprising the step of:
    administering to a patient in need thereof a composition comprising activated charcoal and limestone,
    wherein said symptom is selected from the group consisting of a headache, fatigue, loss of energy, light sensitivity, sound sensitivity, irritated eyes, dry mouth, nausea, vomiting, diarrhea, bloating, cramping, shaking, sweating, dizziness, mood swings, and a hangover.

2. The method of claim 1, wherein said method is administered as a prophylactic treatment.

3. The method of claim 1, wherein said symptom is selected from the group consisting of light sensitivity, sound sensitivity, irritated eyes, vomiting, bloating, cramping, sweating, dizziness, mood swings, and a hangover.

4. The method of claim 1, wherein said symptom is a headache.

5. The method of claim 1, wherein said symptom is fatigue.

6. The method of claim 1, wherein said symptom is loss of energy.

7. The method of claim 1, wherein said symptom is sound sensitivity.

8. The method of claim 1, wherein said symptom is irritated eyes.

9. The method of claim 1, wherein said symptom is dry mouth.

10. The method of claim 1, wherein said symptom is nausea.

11. The method of claim 1, wherein said symptom is vomiting.

12. The method of claim 1, wherein said symptom is diarrhea.

13. The method of claim 1, wherein said symptom is bloating.

14. The method of claim 1, wherein said symptom is cramping.

15. The method of claim 1, wherein said symptom is shaking.

16. The method of claim 1, wherein said symptom is sweating.

17. The method of claim 1, wherein said symptom is dizziness.

18. The method of claim 1, wherein said symptom is mood swings.

19. The method of claim 1, wherein said symptom is a hangover.

* * * * *